US010214575B2

(12) United States Patent
Gilljam et al.

(10) Patent No.: US 10,214,575 B2
(45) Date of Patent: *Feb. 26, 2019

(54) PROCESS FOR THE PURIFICATION OF A GROWTH FACTOR PROTEIN

(71) Applicant: OCTAPHARMA AG, Lachen (CH)

(72) Inventors: Gustav Gilljam, Skogas (SE); Stefan Winge, Arsta (SE); Maya Tiemeyer, Ladenburg (DE)

(73) Assignee: OCTAPHARMA AG, Lachen (CH)

(*) Notice: Subject to any disclaimer, the term of this patent is extended or adjusted under 35 U.S.C. 154(b) by 0 days.

This patent is subject to a terminal disclaimer.

(21) Appl. No.: 15/256,288

(22) Filed: Sep. 2, 2016

(65) Prior Publication Data

US 2017/0051028 A1    Feb. 23, 2017

Related U.S. Application Data

(63) Continuation of application No. 13/638,244, filed as application No. PCT/EP2011/054920 on Mar. 30, 2011, now Pat. No. 9,453,045.

(60) Provisional application No. 61/282,894, filed on Apr. 16, 2010.

(30) Foreign Application Priority Data

Mar. 30, 2010   (EP) ..................................... 10158522

(51) Int. Cl.
| | |
|---|---|
| C07K 1/16 | (2006.01) |
| C07K 1/36 | (2006.01) |
| B01D 15/32 | (2006.01) |
| B01D 15/34 | (2006.01) |
| B01D 15/36 | (2006.01) |
| B01D 15/38 | (2006.01) |
| C07K 14/52 | (2006.01) |
| C07K 14/475 | (2006.01) |
| C07K 14/535 | (2006.01) |
| C07K 14/575 | (2006.01) |

(52) U.S. Cl.
CPC ............ *C07K 14/535* (2013.01); *B01D 15/34* (2013.01); *B01D 15/362* (2013.01); *B01D 15/3828* (2013.01); *B01D 15/3847* (2013.01); *C07K 1/165* (2013.01); *C07K 1/36* (2013.01); *C07K 14/475* (2013.01); *C07K 14/52* (2013.01); *C07K 14/575* (2013.01)

(58) Field of Classification Search
None
See application file for complete search history.

(56) References Cited

U.S. PATENT DOCUMENTS

| | | |
|---|---|---|
| 6,624,295 B1 | 9/2003 | Adams et al. |
| 6,627,737 B1 | 9/2003 | Foster et al. |
| 8,329,871 B2 | 12/2012 | Borgvall et al. |
| 9,453,045 B2* | 9/2016 | Gilljam ................ B01D 15/362 |
| 2008/0207487 A1 | 8/2008 | DeFrees et al. |

FOREIGN PATENT DOCUMENTS

| | | |
|---|---|---|
| CN | 101260145 A | 9/2008 |
| EP | 0 131 740 A2 | 1/1985 |
| EP | 1 707 634 A1 | 10/2006 |
| EP | 1 739 179 A1 | 1/2007 |
| EP | 2-027-875 A1 | 2/2009 |
| WO | WO-2005/082483 A1 | 9/2005 |
| WO | WO-2005/121163 A2 | 12/2005 |
| WO | WO-2006/128497 A1 | 12/2006 |
| WO | WO-2008-073620 A2 | 6/2008 |
| WO | WO-2008/081025 A1 | 7/2008 |
| WO | WO-2009/007451 A1 | 1/2009 |
| WO | WO-2009/024620 A2 | 2/2009 |
| WO | WO-2009-063069 A2 | 5/2009 |
| WO | WO-2009-156430 A1 | 12/2009 |
| WO | WO-2011/121031 A1 | 10/2011 |

OTHER PUBLICATIONS

Bai et al., Renaturation and purification of rhGM-CSF with ion-exchange chromatography, Biotechnology Progress. 2007; 23(5):1138-1142.
Brochier et al., Fast purification process optimizing using mixed-mode chromatography sorbents in pre-packed mini-columns, Journal of Chromatography. 2007; 1177(2): 226-233.
Capto MMC / Data File 11-0035-45 AA, Internet Citation, 2005, URL: http://www.gelifesciences.co.jp/catalog/pdr_attach/11003545AA.pdf.
GE Healthcare Instructions for Capto MMC, Instructions 11-0035-05 AD, Mar. 2005, pp. 1-24, URL: http://www.gelifesciences.com/aptrix/upp00919.nsf/Content/DDE84FA9F53D2925C1257628001D1EBF/$file/11003505AD.pdf.
Kaleas K A et al., Industrial case study: Evaluation of a mixed-mode resin for selective capture of a human growth factor recombinantly expressed in *E. coli*, Journal of Chromatography. 2010; 1217(2):235-242.
Pizarro et al., High-yield expression of human vascular endothelial growth factor VEGF165 in *Escherichia coli* and purification for therapeutic applications, Protein Expression and Purification. 2010; 72(2):184-193.
Rao Dasari Venkata Krishna et al., A purification method for improving the process yield and quality of recombinant human granulocyte colony-stimulating factor expressed in *Escherichia coli* and its characterization, Biotechnology and Applied Biochemistry. US LNKD-DOI: 10.1042/BA20070130, 2008; 50(2).

(Continued)

*Primary Examiner* — Brian Gangle
*Assistant Examiner* — Andrea K McCollum
(74) *Attorney, Agent, or Firm* — Keith G. Haddaway; Kerri M. Patterson; Venable LLP

(57) ABSTRACT

A method of purifying a Growth Factor Protein in a purification sequence employing chromatography is provided. The method comprises performing at least one chromatography step using a multimodal resin, binding the Growth Factor Protein to the multimodal resin at a pH from 4 to 6.2, and eluting the Growth Factor Protein at a pH in the range of from 5.5 to 6.5. The elution of Growth Factor Protein is improved by addition of arginine and/or NaCl in the eluting buffer. Optionally the multimodal resin step is followed by a yeast derived affinity ligand resin step, which results in a purity of the product greater than 90%.

17 Claims, 11 Drawing Sheets

(56) References Cited

OTHER PUBLICATIONS

European Patent Office Examination Report dated Jul. 8, 2013, issued in European Application No. 11711340.7.
European Office Action dated Mar. 4, 2014, issued in European Application No. 11711340.7.
International Search Report issued in Application No. PCT/EP2011/054920, dated Sep. 5, 2011.
Written Opinion issued in Application No. PCT/EP2011/054906 dated Sep. 5, 2011.
Koide et al., Isolation and Characterization of Bovine Factor XI (Plasma Thromboplastin Antecedent), Biochemistry. 1977; 6(10):2279-2286.
Tait et al., Primary Structure Requirements for the Binding of Human High Molecular Weight Kininogen to Plasma Prekallikrein and Factor XI, The Journal of Biological Chemistry. 1987; 262(25):11651-11656.
Saito et al., Partial Purification of Plasma Thromboplastin Antecedent (Factor XI) and its Activation by Trypsin, The Journal of Clinical Investigation. 1973; 52:850-861.
Mashiko et al., Purification of Factor XI and Some Properties of Activated Factor XI from Porcine Plasma, Recent Progress on Kinins. 1992; 38:249-256.
Fujikawa, Historical perspective of factor XI, Thrombosis Research. 2005; 115:441-450.
Burnouf-Radosevich et al., A therapeutic, highly purified factor XI concentrate from human plasma, Transfusion. 1992; 32(9):861-867.
Burnouf et al., Affinity chromatography in the industrial purification of plasma proteins for therapeutic use, Journal of Biochemical and Biophysical Methods. 2001; 49:575-586.
Bouma et al., Human Blood Coagulation Factor XI, The Journal of Biological Chemistry. 1977; 252(18):6432-6437.
International Search Report and Written Opinion in Application No. PCT/EP2011/070257 dated Feb. 21, 2012.
Mashiko H., et al., Factor XI: Purification From Porcine Plasma by Affinity Chromatography and Some Properties of Factor XI and activated Factor XI Biol. Chem. 1944; 481-484 (Abstract Only).
Wolberg et al., Coagulation Factor XI is a Contaminant in Intravenous Immunoglobulin Preparations, American Journal of Hematology. 2000; 65:30-34.
Sekiya et al., Regulation of the tertiary structure and function of Coagulation Factor IX by Magnesium(II) ions, The Journal of Biological Chemistry. 1987; 270(24):14325-14331.
Sigma Aldrich Hyflo Super Cel product sheets: 3 pages total. Retrieved from the Internet on Jan. 22, 2015.
Zhao et al., Characterization of a Heparin Binding Site on the Heavy Chain of Factor XI, The Journal of Biological Chemistry. 1998; 273(47):31153-31159.
Arakawa et al., MEP HyperCel chromatography II: Binding, Washing and elution, Protein Expression and Purification. 2009; 71(2):168-173.
Kohei et al., Review: Why is Arginine Effective in Suppressing Aggregation?, Protein and Peptide Letters. 2005; 12(7):613-619.
Lindsay et al., Purification of recombinant DNA-derived factor IX produced in transgenic pig milk and fractionation of active and inactive subpopulations, J Chrom A. 2004; 1026:149-157.
Harrison et al., The manufacturing process for recombinant Factor IX, Sem Hematol. 1998; 35(Suppl 2): 4-10.
Kaufman et al., Expression, purification, and characterization of recombinant gamma-carboxylated Factor IX synthesized in chinese hamster ovary cells, JBC. 1986; 261:9622-9628.
Roberts P. Virus Inactivation by solvent/detergent treatment using Triton X-100 in a high purity Factor VIII, Biologicals; 2008; 36:330-335.
Burnouf et al., Nanofiltration of plasma-derived biopharmaceutical products, Haemophilia. 2003; 9:24-37.
Parker et al., Multiple vitamin K-dependent coagulation zymogens promote adenovirus-mediated gene delivery to hepatocytes, Blood. 2006; 108:2554-2561.
Butenas et al., Blood Coagulation, Biochemistry. 2002; 67(1):3-12.
Morfini et al., Clinical use of factor VIII and factor IX concentrates, Blood Transfusion. 2013; 11(Suppl 4): s55-63.
International Preliminary Report in Patentability in PCT International Application No. PCT/EP2011/070257 dated May 21, 2013.
Tanaka et al., A chromatographic method for the production of a human immunoglobulin G solution for intravenous use, Brazilian Journal of Medical and Biological Research. 1998; 31:1375-1381.
Office Action issued in European Patent Application No. 11713216.7 dated Nov. 29, 2013.
Dapto Adhere, GE Health Care (28-97078-88AA), Data sheet, 6 pages, available online at: http://wolfson.huji.ac.il/purification/PDF/IonExchange/AMERSHAM_CaptoAdherell.pdf dated Jan. 2007.

* cited by examiner

Silver stained 10% SDS-PAGE: MES buffer was used as running buffer.

PROCESS FOR THE PURIFICATION OF A GROWTH FACTOR PROTEIN

CROSS-REFERENCE TO RELATED APPLICATIONS

This application is a continuation of application Ser. No. 13/638,244, filed Sep. 28, 2012, published Apr. 18, 2013, as US2013/0096279, currently pending, which is a U.S. National Stage of PCT Patent Application No. PCT/EP2011/054920, filed Mar. 30, 2011, which claims the benefit of U.S. Provisional Patent Application No. 61/282,894, filed Apr. 16, 2010, and which claims the benefit of European Patent Application No. 10158522.2, filed Mar. 30, 2010, all of which are incorporated by reference in their entireties herein.

BACKGROUND OF THE INVENTION

The present invention pertains to a process of the purification of a growth factor protein employing chromatography.

The purification of proteins from sources of natural origin is a challenge as the protein of interest is often only present in trace amounts and accompanied by other biopolymers such as lipids, proteins, or even cell fragments. Moreover the proteins of interest are mostly associated with a biological function which is often lost during process steps for its purification.

The arsenal of methods for purifying biopolymers such as proteins is large. Besides precipitation methods chromatographic methods on various kinds of materials are known. Frequently the materials are modified with chemical moieties such as organic ions, cations such as protonated amines or partially or completely alkylated amines. Such materials are used as anion exchangers. But also cation exchangers can be used for purification methods depending on the physical properties of the protein of interest such as shape, molecular weight and in particular its charge. Alternatively or in combination affinity chromatography is employed.

It is known in prior art that one disadvantage with traditional ion exchange chromatography resins (as for example SP-, CM-, Q- or DEAE SEPHAROSE® FF ion exchange chromatography resins) is that the binding of a protein to the resin only can be performed within relatively low salt concentration (conductivity, osmolality etc.), typically in the range of 0.01-0.15M of salt (NaCl etc.) concentration. In certain applications there would be a demand to be able to use the relatively mild purification conditions a ion exchange chromatography step exerts towards the proteins, also directly (without further dilution) to a chromatography resin at somewhat increased ionic strength. An increased ionic strength can be of significant advantage for the protein stability in a protein solution; especially in a crude protein preparation like in the harvest of recombinant produced protein products or in plasma derived products where potential proteases are present in the solution which can affect the target protein negatively. As proteases often work best at physiological conditions (like is the case in most cell systems), i.e approximately pH 7 and a salt concentration of approximately 0.15M.

Proteases could be inhibited by changing the work-up conditions eg by addition of salt and/or change of the pH, however, both these parameters are critical for the performance of a conventional ionic chromatography step and thus often impossible to use in their combination. There is a need to provide a purification method in the course of which conditions to minimise the effects of proteases can be employed.

WO-A2-2008/073620 discloses a manufacturing method for polypeptides that are produced in insect cells using a baculoviral expression system. In one example, the insect cell culture is supplemented with a lipid mixture immediately prior to infection (e.g., one hour prior to infection). The polypeptides are isolated from the insect cell culture using a method that employs anion exchange or mixed-mode chromatography early in the purification process. This process step is useful to remove insect-cell derived endoglycanases and proteases and thus reduces the loss of desired polypeptide due to enzymatic degradation. In another example, mixed-mode chromatography is combined with dye-ligand affinity chromatography in a continuous-flow manner to allow for rapid processing of the insect-cell culture liquid and capture of the polypeptide. In yet another example, a polypeptide is isolated from an insect cell culture liquid using a process that combines hollow fiber filtration, mixed-mode chromatography and dye-ligand affinity in a single unit Operation producing a polypeptide solution that is essentially free of endoglycanase and proteolytic activities. In a further example, the isolated polypeptides are glycopeptides having an insect specific glycosylation pattern, which are optionally conjugated to a modifying group, such as a polymer (e.g., PEG) using a glycosyltransferase and a modified nucleotide sugar.

WO-A2-2009/063069 discloses a process for purifying peptides, in particular but not exclusively, to a process for removing endotoxins from a peptide solution, to a kit comprising reagents for said process and to the purified peptide obtained by said process.

Dasari Venkata Krishna Rao et al. discloses a purification method employing a process control-strategy developed for improving the yield of rhG-CSF (recombinant human granolocyte colony-stimulating factor). A purity of ≥99% with an overall yield of 2.18 g/l was achieved in the present study. Analysis of the product during purification indicated that detergents removed 72% of LPS (lipopolysaccharides) and 98% of HCPs (host cell proteins) without removing nucleic acid. Cysteine concentration was a key parameter in protein refolding. The bed height and HETP (height equivalent theoretical plates) value in the SEC (size-exclusion chromatography) column was evaluated and its impact on the resolution was studied. Formulation during SEC was found to be crucial for increasing the product yields with saving of time and process costs.

Quan Bai et al. studies the renaturation and purification of recombinant human granulocyte macrophage colony stimulation factor (rhGM-CSF) expressed in *Escherichia coli* with strong anion-exchange chromatography (SAX). The effects of pH values, ratios of concentrations of GSH/GSSG, and urea concentrations in the mobile phase on the renaturation and purification of rhGM-CSF with SAX were investigated, respectively. The results show that the above three factors have remarkable influences on the efficiency of renaturation and mass recovery of rhGM-CSF. The addition of GSH/GSSG in the mobile phase can improve the formation of correct disulfide bonds in rhGM-CSF so that its renaturation yield increases. In addition, to enhance the mass recovery of rhGM-CSF with SAX, the low concentration of urea was added in the mobile phase to prevent denatured protein aggregation. Under the optimal conditions, rhGM-CSF was renatured with simultaneous purification on SAX column within 30 min only by one step.

Shelly A. Pizarro reports about a vascular endothelial growth factor (VEGF165) which is a potent mitogen that induces angiogenesis and vascular permeability in vivo and has demonstrated potential in therapeutic applications for accelerating wound healing. The process described in this report involves a bacterial expression system capable of producing approximately 9 g of rh VEGF per liter of broth and a downstream purification process of protein refolding and three chromatography steps prior to formulation of the drug substance. A high cell density (HCD) fed-batch fermentation process was used to produce rhVEGF in perisplasmic inclusion bodies. The inclusion bodies are harvested from the cell lysate and subjected to a single-step protein solubilization and refolding operation to extract the rhVEGF for purification. Overall recovery yields observed during development, including refolding and chromatography, were 30±6%. Host cell impurities are consistently cleared below target levels at both laboratory and large-scale demonstrating process robustness. The structure of the refolded and purified rhVEGF was confirmed by mass spectrometry. N-terminal sequencing, and tryptic peptide mapping while product variants were analyzed by multiple HPLC assays.

Kimberly A. Kaleas discloses that mixed-mode chromatography resins are gaining popularity as purification tools for challenging feedstocks, and discloses the development of an industrial application to selectively capture recombinant human vascular endothelial growth factor (rhVEGF) on CAPTO® MMC from an alkaline feedstock. CAPTO® MMC resin contains a ligand that has the potential to participate in ionic, hydrophobic, and hydrogen bonding interactions with proteins and is coupled to a highly cross-linked agarose bead matrix. VEGF is a key growth factor involved in angiogenesis and has therapeutic applications for wound healing. It is expressed in *Escherichia coli* as inclusion bodies. Solids are harvested from the cell lysate, and the rhVEGF is solubilized and refolded and pH 9.8 in the presence of urea and redox agents. The unique mixed mode characteristics of CAPTO® MMC enabled capture of this basic protein with minimal load conditioning and delivered a concentrated pool for downstream processing with >95% yields while reducing host cell protein content to <1.2%. This study explores the impact of loading conditions and residence time on the dynamic binding capacity as well as the development of elution conditions for optimal purification performance. After evaluating various elution buffers, L-arginine HCl was shown to be an effective eluting agent for rhVEGF desorption from the CAPTO® MMC mixed-mode resin since it successfully disrupted the multiple interactions between the resin and rhVEGF. The lab scale effort produced a robust chromatography step that was successfully implemented at commercial manufacturing scale.

One object of the invention was to avoid the drawbacks of the purification processes of a growth factor protein of prior art by providing a novel process. According to the invention the object is accomplished by a process of purifying a growth factor protein selected from the group consisting of Colony Stimulating Factor (CSF) such as G-CSF (Granulocyte Colony Stimulating Factor) or granulocyte-macrophage CSF (GM-CSF), interleukin 3 (IL-3), Hepatocyte growth factor, Epidermal growth factor and fibroblast growth factor (acid) in a purification sequence employing chromatography wherein at least one chromatography is performed using a multimodal resin the Growth Factor Protein binds to the multimodal resin at a pH between 4 to 6.2, and the Growth Factor Protein is eluting from the multimodal resin at a pH >6.3.

The invention provides a process in which advantageously the effects of proteases can be minimised. Making it possible to add salt and/or change the pH in crude protein sample with potential proteases present which could degrade the target protein and to process the protein solution without any further measures and bind the target protein to a mixed mode chromatography resin and thus providing a optimized step for concentration and purification of the target protein in a crude sample, making it suitable for further purification downstream using a specific affinity chromatography step directed towards the target protein, with reduced protease and/or DNA content during the downstream processing. This is of specific importance, to avoid degradation of the target protein during purification, making the combination of multimodal chromatography as a capture step in a crude protein solution.

In one embodiment, the chromatography on multimodal resins is combined with a yeast derived affinity ligand chromatography step. The chromatographic step employing the yeast derived affinity ligand, is especially suitable for the purification of the target protein in high yield and an unchanged molecule integrity (degradation etc.).

The Growth Factor Protein is a Colony Stimulating Factor (CSF) such as G-CSF (Granulocyte Colony Stimulating Factor). This is a member of the hemopoietic regulatory glycoproteins which are involved in the growth and differentiation of hemopoietic cells from stem cells. Growth Factor Proteins are granulocyte-macrophage CSF (GM-CSF), interleukin 3 (IL-3), Hepatocyte growth factor, Epidermal growth factor and fibroblast growth factor (acid). The Growth Factor Proteins all show an IP≤6. In a further embodiment of the invention the multimodal resin comprises moieties bound to a matrix and the moieties are able to interact with the Growth Factor Protein in a mixture by ionic interactions and other types of interactions such as hydrogen bonding, hydrophobic and thiophilic interactions.

In a further embodiment of the invention the affinity ligand is a yeast derived $F_{ab}$ fragment directed towards the growth factor protein.

In a further embodiment of the invention the multimodal resin step is processed to capture the Growth Factor Protein from a crude protein solution whereafter processing the resulting multimodal chromatography resin eluate to the yeast derived affinity ligand chromatography step and after elution of the Growth Factor protein from said affinity chromatography step, exerting a purity of more than approximately 90% in relation to proteins and DNA.

In another further embodiment of the invention the multimodal resin step and the yeast derived affinity ligand chromatography step is combined with other chromatography purification step to exert a purity of more than 99% in the final Growth Factor Protein product.

In still another embodiment of the invention the mixture comprising the Growth Factor Protein is a solution.

In yet another embodiment of the invention the Growth Factor Protein is a recombinant Growth Factor Protein.

In yet another embodiment of the invention the Growth Factor Protein is in a crude protein solution including potentially proteases which can degrade the product.

In another embodiment the Growth Factor Protein is eluted by a pH change >pH 6.3.

In a further embodiment of the invention the elution is performed with an elution agent comprising an amino acid having a basic side chain and/or high ionic strength. Alternatively or in combination the elution can also be performed by a pH change. The pH change is performed by adjusting the pH of the elution buffer with for example sodium hydroxide or acetic acid to desired pH and thereafter applying the buffer to the multimodal resin and the ionic strength adjustment can be performed by adding salt, in the elution buffer composition before applying to the multimodal resin, for example salts included in the Hofmeister series, for example sodium chloride and potassium chloride.

According to the invention the concentration of the elution agent is in particular in the range of from about 0.1M to about 2 M According to another embodiment of the invention the Growth Factor Protein binds to the multimodal resin at about pH 6.0 whereas the Growth Factor Protein is eluted from the multimodal resin at a pH about 6.5 or higher in particular at about pH 7.0.

In a further embodiment of the invention a buffering substance is used comprising preferably at least one of the substances selected from the group consisting of sodium citrate, histidine, 2-(4-(2-Hydroxyethyl)-1-piperazinyl)-ethane sulfonic acid (HEPES), 2-(N-Morpholino)ethane sulfonic acid (MES), Tris base and sodium acetate in particular in a range of about pH 4 to about pH 8. In the process of the invention one non-ionic detergent can be present in any of the buffers used, which non-ionic detergent is in particular selected from the group consisting of Polysorbates (Polysorbate 20, 40, 60, 80) and PLURONIC® F68.

In a further embodiment of the process of the invention the amino acid can be selected from the group of amino acid having a basic side chain including arginine, lysine and histidine; the organic salts can be selected from the group of KCl and NaCl In another embodiment of the invention a wash step is performed at a pH in the range of about pH 4 to about pH 6, before eluting the Growth Factor Protein from the multi modal resin, characterised that the wash buffer includes washing agents comprising an amino acid having a basic side chain and/or high ionic strength, the ionic strength adjustment can be performed by adding salt, in the wash buffer composition before applying to the multimodal resin, for example salts included in the Hofmeister series, for example sodium chloride and potassium chloride According to the invention the concentration of the washing agent is in particular in the range of from about 0.1M to about 2M It can be advantageous to apply the washing buffer to the multimodal resin, to wash away contaminants (proteases, DNA etc.) and retain the Growth Factor Protein, before the Growth Factor Protein is released.

Particularly, the concentration of the amino acid which is positively charged at a pH 6-8 is present in an amount of up to 2M in the wash buffer at a pH of <6.3. Typically, the amount of arginine is in the range of 0.1-1.0M, in particular 0.5M in the wash buffer.

In the elution buffer with a pH≥6.3 the amount of arginine is typically in the range of 0.1 to 2M, in particular 0.5M.

In the elution buffer with a pH≥6.3, sodium chloride is included in a range of 0.1-2.0M, in particular in a range from 0.1 to 1M.

In the wash buffer with a pH≤6.3, sodium chloride is included in a range of 0.1-2.0M, in particular in a range from 0.1 to 1M.

The amount of non-ionic detergent is typically in the range of 0.001 to 1%, in particular in the buffers for multimodal chromatography 0.02%.

The multimodal chromatography resin which can be employed according to the invention may contain at least one of the following moieties:

a. a positively charged N-Benzyl-N-methyl ethanolamine ligand,
 b. a negatively charged 2-(benzoylamino) butanoic acid ligand,
 c. a phenylpropyl ligand,
 d. a N-hexyl ligand,
 e. a 4-Mercapto-Ethyl-Pyridine ligand,
 f. a 3-((3-methyl-5-((tetrahydrofuran-2-ylmethyl)-amino)-phenyl)-amino)-benzoic acid ligand or combinations thereof.

In particular, a multimodal chromatography resin for use according to the present invention is selected from the following commercially available resins HEP Hypercel™; PPA Hypercel™; CAPTO® Adhere™; CAPTO® MMC™; MEP Hypercel™.

In another embodiment of the present invention the purification sequence may further comprise pathogen removal/inactivation steps comprising a chemically based inactivation step, a size based removal step, chromatography steps or combinations thereof which steps are based on different physiological properties directed to the pathogen to be removed.

In a particular embodiment the process of the invention the purification sequence further comprises the following steps:
 1. a cation multimodal resin such as CAPTO® MMC;
 2. a chemically based inactivation step for enveloped viruses in particular the solvent/detergent-inactivation employing tri-n-butyl phosphate and Triton X-100 as disclosed in EP-A-131 740;
 3. an affinity resin based on a ligand expressed in yeast;
 4. a cation exchanger such as SP SEPHAROSE® or Resource S;
 5. a pathogen filtration removal step with a mean pore sized of about 20 nm such as PLANOVA® 20N;
 6. a buffer exchange and/or concentrating step such as ultra filtration with an approximate cut off of 1-5 kDa;
 7. a size exclusion chromatography resin such as SUPERDEX® 75.

Figure 1:
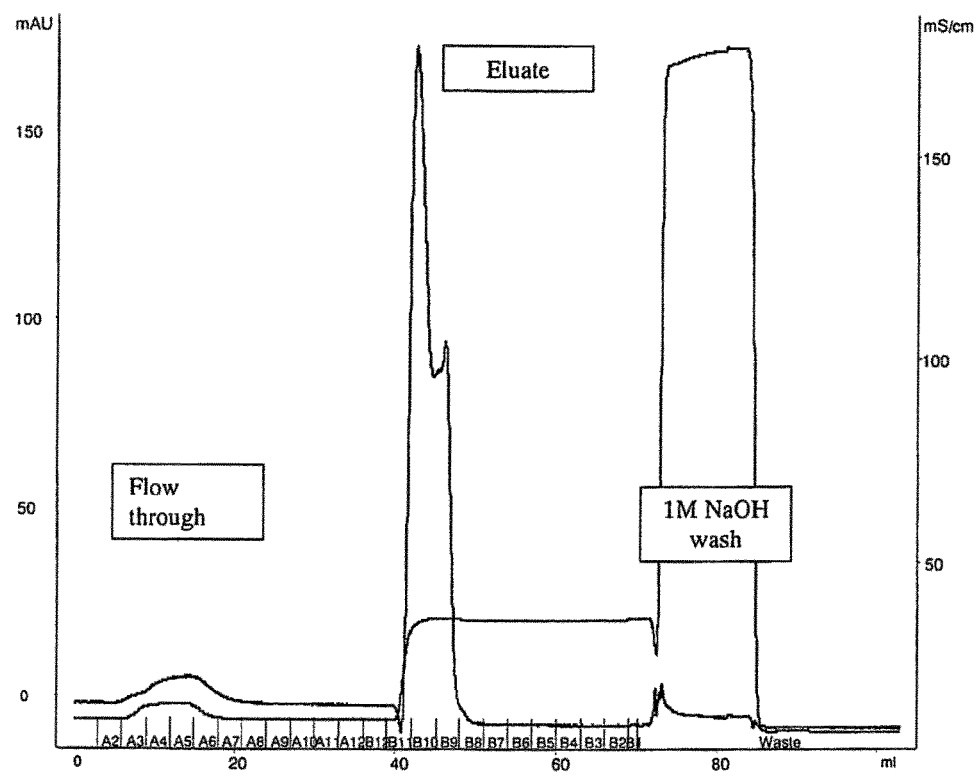
FIG. 1 shows a chromatogram of the G-CSF purification on a CAPTO® MMC column at pH 4.0 using a sodium acetate buffer.

The invention is further described by the following non-limiting examples which have been exemplified by G-CSF purification.

EXAMPLES

Description of Analytical Methods
Determination of G-CSF Content by G-CSF Specific ELISA The principle of an Enzyme Linked Immunoabsorbent Assay (ELISA) is the quantification of a protein (antigen) by its specific binding to antibodies against this protein. The G-CSF quantification was performed by use of a sandwich ELISA, based on the G-CSF Duo Set ELISA (R&D Systems, Cat No DY214). As calibration standard *E. coli* derived recombinant human G-CSF (R&D systems, Cat No. 214-CS-005, 0.015-1 ng/ml) was applied. The capturing antibody (mouse anti-human G-CSF) was bound to the wells of a 96-well microtiter plate. After capturing of the G-CSF antigen and a wash step, biotinylated detection antibody (goat anti-human G-CSF) was bound to the G-CSF antigen. After a second wash step, streptavidin conjugated to Horse Radish Peroxidase (Streptavidin-HRP) was applied, which bounds to the biotinylated detection antibody. For quantification the peroxidase substrate Tetramethylbenzidine (TMB) in presence of hydrogen peroxide was added and a blue colour develops. After stopping the reaction with sulphuric acid, a stable yellow dye develops. The concentration of yellow dye is proportional to the amount of bound peroxidise and thus proportional to the amount of G-CSF antigen. The concentration of the dye is measured photometrically at 450 nm. The G-CSF concentration in the unknown samples was calculated from the recombinant human G-CSF standard curve, which always gave a linear correlation coefficient (r) of >0.99.

Determination of G-CSF Content by Reversed-Phase (RP) HPLC

RP-HPLC involves the separation of proteins based on their polarity; the retention of the protein molecules is governed by hydrophobic interactions between the nonpolar moiety of the solute molecules and the non polar stationary phase of the HPLC column. An HPLC system (DIONEX® Ultimate 3000), equipped with a UV detector and a Jupiter C18, 300 A, 5 μm, 4.6×150 mm column (PHENOMENEX®, Cat. no. 00F-4053-EO) was used for protein determination. The column, run at 20±5° C., was equilibrated with 0.1% (v/v) trifluoroacetic acid (TFA) in water (mobile phase A). For elution, 0.1% (v/v) TFA in acetonitrile (mobile phase B) was used in the linear gradient (0-5 min 5% B, 5-12 min 55% B, 12-17 min 100% B, 17-22 min 5% B) with a flow rate of 1.0 ml/min. The sample load was 30 μg per injection in a total injection volume of maximal 100 μL. Detection was carried out by measuring the UV absorbance at 214 nm. Filgrastim CRS from Ph.Eur 2.5-40 μg (2.5-5-10-20-40 μg) was used for the standard curve. The Filgrastim CRS standard was pre-diluted in water for laboratory use (WFL) to a concentration of 0.4 mg/ml. A pre-dilution of the samples in WFL was performed to a injection amount of 30 μg, if necessary. The G-CSF content in the unknown samples was calculated from the Filgrastim CRS standard curve, which always gave a linear correlation coefficient (r) of >0.99.

Purity Determination by Reversed-Phase (RP) HPLC

The method and devices used for purity determination by RP-HPLC is equivalent to the method for determination of G-CSF content. The purity of the G-CSF containing solution [%] was calculated by setting the peak area of the G-CSF peak in ratio to the total peak area.

Purity Determination & Molecular Weight Distribution by SDS-PAGE

SDS polyacrylamide gel electrophoresis (SDS-PAGE) involves the separation of proteins based on their size. The purity determination and analysis of molecular weight distribution for G-CSF containing samples was performed under reduced conditions. For this purpose Tris-Tricine gradient gels (10-20%, from Anamed, Cat No. TR12012) and Tris-HCl gradient gels (10-20%, from Biorad, Cat No. 345-0043) were used. For the Tris-Tricine gradient gels the Polypeptide SDS-PAGE Molecular Weight Standard from BioRad (Cat No. 161-0326; 1.4-26.6 kDa) was applied as molecular weight standard; for the Tris-HCl gradient gels the Precision Plus Protein All Blue Standard from Biorad (Cat No. 161-0373, 10-250 kDa) was applied. The protein bands separated by electrophoresis are visualized by silver or coomassie staining. *E. coli* derived recombinant human G-CSF (non glycosylated, R&D systems, Cat No. 214-CS-005) the glycosylated, CHO derived commercial product Granocyte (Chugai) were used as G-CSF references (control samples). The evaluation of molecular weight and purity is done visually by judging the appearances of the standards, reference (control sample) and analysed samples.

Recombinant G-CSF

Production of G-CSF containing cell suspension and purification.

Cells

The cell line used is a derivative of human embryonic kidney cell 293 (HEK 293), which was adapted to serum-free growth. This host, HEK 293F, was stably transfected with an expression cassette carrying the cDNA coding sequence for G-CSF. The strong promoter was used for the cassette. The general process is also described in EP 1739179 (Schröder et al).

Cultivation Method

The cells were cultivated in serum-free medium in general equipment and according to general methods well known in the art, for example shaken or stirred cultures in t-flasks, shaker flasks and bioreactors (disposable systems and conventional stirred tanks) run as batch, fed-batch, perfusion or continuous chemostat cultures (Freshney, R I (2000), Culture of animal cells: a manual of basic technique, 4$^{th}$ ed, Wiley-Liss; Spier, R E ed (2000), Encyclopedia of cell technology, Wiley, New York; Enfors, S—O and Häggström, L (2000), Bioprocess technology: fundamentals and applications, Högskoletryckeriet, Royal Institute of Technology, Stockholm; Vinci, V A and Parekh, S R (2003), Handbook of industrial cell culture: mammalian, microbial, and plant cells, Humana Press, USA). Typically, perfusion of medium was used to increase cell numbers and product titers beyond standard batch culture levels. The product yield and the amount of host cell proteins differ depending on the cultivation mode:

the product titre will typically increase with cell numbers
the total protein content and DNA content will typical increase with cell numbers
the total protein content and DNA content can also increase with culture longetivity
batch cultures accumulate protein and DNA; nothing is externally added, nothing is removed
perfusion processes rinse cell cultures from metabolites, protein, DNA and other impurities; filters or cell centrifuges were typically used for cell retention.

The recombinant product is released from the cells and the cell suspension or the cell suspension supernatant is the harvest. The properties of the harvest (product titres and impurities as mentioned above) differ depending on the cultivation mode used.

The cell suspension has been used in some of the below described G-CSF examples.

Purification Method

The recombinant product is released from the cells and the cell suspension or the cell suspension supernatant is the harvest. The purification applied comprises a 4-step purification. Cation exchange chromatography (SP SEPHAROSE® Fast Flow (FF)) was used for the capturing step of G-CSF from the cell culture supernatant, followed by a zinc based immobilized metal affinity chromatography (IMAC) step (Zn-IDA chelating SEPHAROSE® Fast Flow (FF)), a second cation exchange chromatography step (Resource S) for polishing and a size exclusion chromatography step (SUPERDEX® 75) as final step.

Preparation of G-CSF Containing Cell Culture Supernatant

Prior to the capturing step the G-CSF concentration of the supernatant batches [mg/L] was determined by a G-CSF specific ELISA in order to verify the total G-CSF amount [mg]. The frozen supernatant (−80° C.) was thawed in a water bath adjusted to 20±5° C. Afterwards the supernatant was centrifuged at 9000×g for 15 minutes at 4° C. and then additionally filtered using 0.2 μg filter units. The pH of the filtered supernatant was adjusted to pH 4.0 using acetic acid.

Capturing Step (SP SEPHAROSE® FF)

An XK 16/20 column was packed with 10 ml of SP SEPHAROSE® FF material (1 column volume (CV)=10 ml). The SP SEPHAROSE® FF resin was obtained from GE Healthcare (Cat No. 17-0729-01).

The equilibration was performed with 3 CV of the equilibration buffer (20 mM sodium acetate, 100 mM sodium chloride, 0.02% TWEEN® 20, pH4.0) followed by loading of the starting material with a flow rate of 2.5 ml/min. The following wash step was performed with the same buffer and flow rate, using 5 CV. The elution was performed with an elution buffer containing 20 mM sodium acetate, 1 M sodium chloride, 0.02% TWEEN® 20, pH4.0, applying a linear gradient from 0% to 40% elution buffer within 8 CV at a flow rate of 2.5 ml/min, followed by a step elution with 100% elution buffer with 5 CV.

The G-CSF concentration of the eluate pool, collected from the linear gradient elution, was analysed by a G-CSF specific ELISA.

IMAC Step (Zn-IDA Chelating SEPHAROSE® FF)

An XK 16/20 column is packed with 10 ml of Chelating SEPHAROSE® FF which is charged by 2 ml 0.2 M ZnCl$_2$ (1 column volume (CV)=10 ml). The Chelating SEPHAROSE® FF resin was obtained from GE Healthcare (Cat No. 17-0575-01).

Prior to loading the pH of the IMAC column load (SP SEPHAROSE® FF eluate) was adjusted to pH 8.0 by NaOH).

The equilibration was performed with 3 CV of the equilibration buffer (20 mM Tris/HCl, 150 mM NaCl, pH 8.0) followed by loading of the SP SEPHAROSE® FF eluate with a flow rate of 2 ml/min. The following wash step was performed with the same buffer and flow rate, using 2 CV.

The elution was performed with an elution buffer containing 20 mM Tris/HCl, 150 mM NaCl, pH 4.0, applying a linear gradient from 0% to 100% elution buffer within 3 CV at a flow rate of 1 ml/min. A gradient delay with 100% elution buffer was applied afterwards with 4 CV.

The G-CSF concentration of the eluate pool, collected from the elution with 100% elution buffer, was analysed by a G-CSF specific ELISA.

Polishing Step (Resource S)

A pre-packed ResourceS column (CV=6 ml) from GE Healthcare (Cat No. 17-1180-01) column is equilibrated with 5 CV equilibration buffer (20 mM sodium acetate, 0.02% TWEEN® 20, pH 4.0) at a flow rate of 4 ml/min. Prior to purification the IMAC eluate must be adjusted pH to 4.0 with acetic acid and diluted 5-times using the equilibration buffer.

The wash step was performed with 10 CV of the equilibration buffer at a flow rate of 4 ml/min.

The elution was performed with an elution buffer containing 20 mM sodium acetate, 1 M NaCl, 0.02% TWEEN® 20, pH 4.0, applying a linear gradient from 0% to 100% elution buffer within 20 CV at a flow rate of 2 ml/min.

The G-CSF concentration of the eluate pool, collected from the linear gradient elution with 50-85% elution buffer, was analysed by a G-CSF specific ELISA.

Size exclusion chromatography step (SUPERDEX® 75)

For the size exclusion step a pre-packed Hiload 26/60 SUPERDEX® 75 Prep Grade column was used (GE Healthcare Cat No. 17-1044-01, CV=320 ml). The column was equilibrated with 1 CV buffer (20 mM sodium acetate, 200 mM NaCl, 0.02% TWEEN® 20, pH 6.5) followed by loading of the ResourceS eluate at a flow rate of 2.5 ml/min and a maximum loading volume of 4% CV.

The G-CSF concentration of the eluate pool was analysed by a G-CSF specific ELISA and by Reversed Phase (RP)-HPLC. The purity of the final purification fraction is analysed by use of RP-HPLC, Size Exclusion (SE)-HPLC and SDS-PAGE and is typically >95%.

The size exclusion eluate has been used in some of below described G-CSF examples.

Purification of rhG-CSF Using CAPTO® MMC Resin as Capture Step.

Example 1 (Experiment 1)

Start Material

Purified rhG-CSF was diluted in an equilibration buffer to lower the total protein concentration and to achieve a more convenient volume prior to be loaded on a CAPTO® MMC column. The rhG-CSF was prior to dilution dissolved in 20 mM sodium acetate, 0.5M NaCl, 0.02% TWEEN® 20, pH 4.0.

Chromatographic Resin and Column

CAPTO® MMC, a mixed mode resin from GE Healthcare (cat no. 17-5317), was used as capture step for the rhG-CSF molecule. CAPTO® MMC is a weak cationic resin with hydrophobic and thiophilic interactions and hydrogen bonding. A TRICORN® 5/150 column (GE Healthcare) was packed with CAPTO® MMC resin to a bed height of 15 cm. The column volume (CV) of CAPTO® MMC was 3 ml.

Buffers

Equilibration buffer: 20 mM sodium acetate, 0.1M NaCl, 0.02% Polysorbate 80, pH 4.0

Eluting buffer: 20 mM sodium citrate, 0.1M NaCl, 0.5M arginin mono hydrochloride, 0.02% Polysorbate 80, pH 7.0.

Experimental Setup

The column was equilibrated with equilibration buffer followed by loading the start material at a flow rate of 1 ml/min. This was followed by a wash step with the equilibration buffer and then the column was eluted using the eluting buffer. Samples were withdrawn and analysed for rhG-CSF by a HPLC method. As seen in Table 1 no G-CSF was found in the flow through fraction. The eluting buffer contained 0.5M arginine mono hydrochloride and the pH was altered to 7.0. The recovery of G-CSF was 89% and the elution profile was a more concentrated peak. The column was after the elution cleaned in place with a 1M NaOH solution. A very small peak was visible from the 1M NaOH wash of the column. The chromatogram is showed in FIG. 1.

TABLE 1

| Sample | Volume ml | rhG-CSF µg/ml | Total rhG-CSF µg | Yield % |
|---|---|---|---|---|
| Start material | 8.71 | 111 | 966.8 | 100 |
| Flow through and equil. wash | 18 | 0 | 0 | 0 |
| Eluate | 12 | 72 | 864 | 89 |

Conclusion

All loaded G-CSF bound to CAPTO® MMC at pH 4.0. A high (89%) yield was obtained in the elution fraction that was collected in three column volumes. The elution buffer had a pH of 7.0 and 0.5M arginine mono hydrochloride was included.

Figure Legend FIG. 1.

Experiment 1; A chromatogram of the G-CSF purification on a CAPTO® MMC column at pH 4.0 using a sodium acetate buffer. The absorbance at 280 nm (mAU) and the conductivity (mS/cm) measured are presented in the figure. The column was eluted using a buffer with pH 7.0 containing 0.5M arginine mono hydrochloride. A double peak was obtained by the elution. The double peak was collected as one fraction.

Example 2 (Experiment 2)

Start Material

Purified rhG-CSF was diluted in an equilibration buffer to lower the total protein concentration and to achieve a more convenient volume prior to be loaded on a CAPTO® MMC column. The rhG-CSF was prior to dilution dissolved in 20 mM sodium acetate, 0.5M NaCl, 0.02% TWEEN® 20, pH 4.0.

Chromatographic Resin and Column

CAPTO® MMC, a mixed mode resin from GE Healthcare (cat no. 17-5317), was used as capture step for the rhG-CSF molecule. CAPTO® MMC is a weak cationic resin with hydrophobic and thiophilic interactions and hydrogen bonding. A TRICORN® 5/150 column (GE Healthcare) was packed with CAPTO® MMC resin to a bed height of 15 cm. The column volume (CV) of CAPTO® MMC was 3 ml.

Buffers

Equilibration buffer: 20 mM sodium acetate, 0.1M NaCl, 0.02% Polysorbate 80, pH 4.0

Eluting buffer: 20 mM sodium citrate, 0.1M NaCl, 0.02% Polysorbate 80, pH 7.0.

Experimental Setup

The column was equilibrated with equilibration buffer followed by loading the start material at a flow rate of 1 ml/min. This was followed by a wash step with the equilibration buffer and then the column was eluted using the eluting buffer. Samples were withdrawn and analysed for rhG-CSF by a HPLC method. As seen in Table 2 no rhG-CSF was found in the flow through. The eluting buffer had a pH of 7.0. More than 90% of the rhG-CSF loaded onto the CAPTO® MMC column was found in the eluted fraction. The elution peak was broader than in experiment 1, where arginin was included in the elution buffer. The elution volume was doubled.

TABLE 2

| Sample | Volume ml | rhG-CSF µg/ml | Total rhG-CSF µg | Yield % |
|---|---|---|---|---|
| Start material | 8.92 | 77.47 | 691 | 100 |
| Flow through and equil. wash | 30 | 0 | 0 | 0 |
| Eluate | 24 | 26.07 | 626 | 90.5 |

Conclusion

Recombinant human G-CSF (rhG-CSF) binds to the CAPTO® MMC resin at pH 4 and could be eluted at pH 7 in a solution buffered with sodium citrate.

Example 3 (Experiment 3)

Start Material

Purified rhG-CSF was diluted in an equilibration buffer to lower the total protein concentration and to achieve a more convenient volume prior to be loaded on a CAPTO® MMC column. The rhG-CSF was prior to dilution dissolved in 20 mM sodium acetate, 0.5M NaCl, 0.02% TWEEN® 20, pH 4.0.

Chromatographic Resin and Column

CAPTO® MMC, a mixed mode resin from GE Healthcare (cat no. 17-5317), was used as capture step for the rhG-CSF molecule. CAPTO® MMC is a weak cationic resin with hydrophobic and thiophilic interactions and hydrogen bonding. A TRICORN® 5/150 column (GE Healthcare) was packed with CAPTO® MMC resin to a bed height of 15 cm. The column volume (CV) of CAPTO® MMC was 3 ml.

Buffers

Equilibration buffer: 20 mM sodium acetate, 0.1M NaCl, 0.02% Polysorbate 80, pH 4.0

Eluting buffer: 20 mM HEPES, 0.3M NaCl, 0.02% Polysorbate 80, pH 7.0.

Experimental Setup

Figure 2:
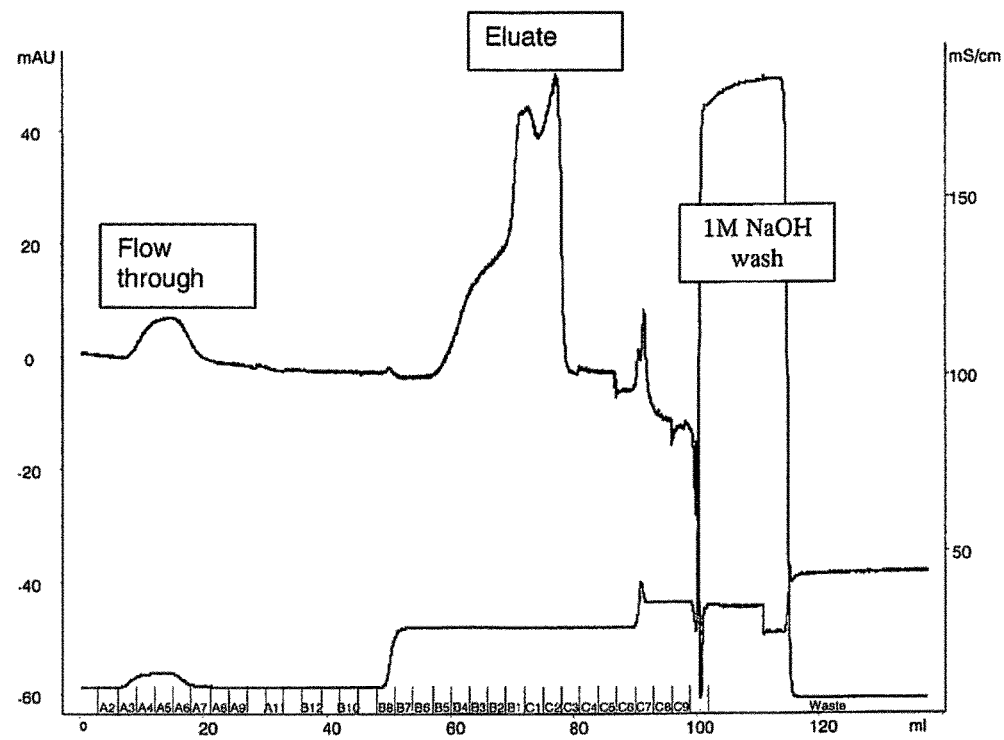
FIG. 2 shows a chromatogram of the G-CSF purification on a CAPTO® MMC column at pH 4.0 using a sodium acetate buffer.

The column was equilibrated with equilibration buffer followed by loading the start material at a flow rate of 1 ml/min. This was followed by a wash step with the equilibration buffer and then the column was eluted using the eluting buffer. Samples were withdrawn and analysed for rhG-CSF by a HPLC method. As seen in Table 3 no rhG-CSF was found in the flow through. The eluting buffer had a pH of 7.0 and the NaCl concentration was elevated to 0.3M compared to in experiment 2. All rhG-CSF loaded onto the CAPTO® MMC column was found in the eluted fraction. The chromatography profile is shown in FIG. 2. A broad elution peak was obtained, and the whole elution peak was collected as one elution fraction.

TABLE 3

| Sample | Volume ml | rhG-CSF µg/ml | Total rhG-CSF µg | Yield % |
|---|---|---|---|---|
| Start material | 8.8 | 71.2 | 627 | 100 |
| Flow through and equil. wash | 30 | 0 | 0 | 0 |
| Eluate | 24 | 27.1 | 650 | 103.7 |

Conclusion rhG-CSF binds to CAPTO® MMC resin at pH 7 and was eluted to 100% at pH 7 when 0.3M NaCl was included in the elution buffer. The elution volume was large, twice the volume compared to if arginin was included in the elution buffer. This means that 0.3M NaCl does not have the same eluting effect on G-CSF from a CAPTO® MMC resin as 0.5M arginine.

Figure Legend FIG. 2.

Experiment 3; A chromatogram of the G-CSF purification on a CAPTO® MMC column at pH 4.0 using a sodium acetate buffer. The absorbance at 280 nm (mAU) and the conductivity (mS/cm) measured are presented in the figure. The column was eluted using a buffer with pH 7.0 containing 0.3M NaCl. A double peak was obtained by the elution. The broad double peak was collected as one fraction.

Example 4 (Experiment 4)

Start Material

Purified rhG-CSF was diluted in an equilibration buffer to lower the total protein concentration and to achieve a more convenient volume prior to be loaded on a CAPTO® MMC column. The rhG-CSF was prior to dilution dissolved in 20 mM sodium acetate, 0.5M NaCl, 0.02% TWEEN® 20, pH 4.0.

Chromatographic Resin and Column

CAPTO® MMC, a mixed mode resin from GE Healthcare (cat no. 17-5317), was used as capture step for the rhG-CSF molecule. CAPTO® MMC is a weak cationic resin with hydrophobic and thiophilic interactions and hydrogen bonding. A TRICORN® 5/150 column (GE Healthcare) was packed with CAPTO® MMC resin to a bed height of 15 cm. The column volume (CV) was 3 ml.

Buffers

Equilibration buffer: 20 mM sodium acetate, 0.1M NaCl, 0.02% Polysorbate 80, pH 4.0

Eluting buffer: 20 mM sodium citrate, 0.5M arginine mono hydrochloride, 0.02% Polysorbate 80, pH 4.0.

Experimental Setup

The column was equilibrated with equilibration buffer followed by loading the start material at a flow rate of 1 ml/min. This was followed by a wash step with the equilibration buffer and then the column was eluted using the eluting buffer. Samples were withdrawn and analysed for rhG-CSF by a HPLC method. As seen in Table 4 no rhG-CSF was found in the flow through. The eluting buffer was altered to a buffer containing arginine and no sodium chloride and the pH was 4.0. No rhG-CSF was found in the eluted fraction.

TABLE 4

| Sample | Volume ml | rhG-CSF µg/ml | Total rhG-CSF µg | Yield % |
|---|---|---|---|---|
| Start material | 9 | 69.4 | 625 | 100 |
| Flow through and equil. wash | 27 | 0 | 0 | 0 |
| Eluate | 27 | 0 | 0 | 0 |

Conclusion rhG-CSF could not be eluted from the CAPTO® MMC resin only by adding 0.5M arginine mono hydrochloride to the buffer, without changing the pH. This can work as a wash step.

Example 5 (Experiment 5)

Start Material

Purified rhG-CSF was diluted in an equilibration buffer to lower the total protein concentration and to achieve a more convenient volume prior to be loaded on a CAPTO® MMC column. The rhG-CSF was prior to dilution dissolved in 20 mM sodium acetate, 0.5M NaCl, 0.02% TWEEN® 20, pH 4.0.

Chromatographic Resin and Column

CAPTO® MMC, a mixed mode resin from GE Healthcare (cat no. 17-5317), was used as capture step for the rhG-CSF molecule. CAPTO® MMC is a weak cationic resin with hydrophobic and thiophilic interactions and hydrogen bonding. A TRICORN® 5/150 column (GE Healthcare) was packed with CAPTO® MMC resin to a bed height of 15 cm. The column volume (CV) of CAPTO® MMC was 3 ml.

Buffers

Equilibration buffer: 20 mM sodium acetate, 0.1M NaCl, 0.02% Polysorbate 80, pH 4.0

Eluting buffer: 20 mM sodium citrate, 0.1M NaCl, 1M arginin mono hydrochloride, 0.02% Polysorbate 80, pH 4.0.

Experimental Setup

Figure 3:
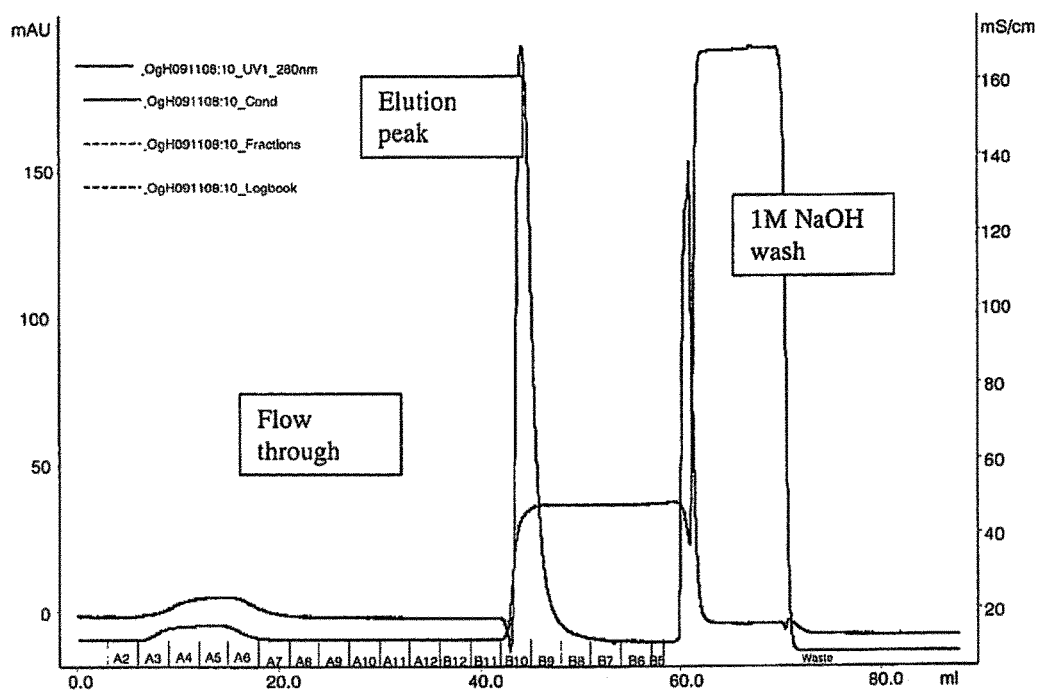
FIG. 3 shows a chromatogram of the G-CSF purification on a CAPTO® MMC column at pH 4.0 using a sodium acetate buffer.

The column was equilibrated with equilibration buffer followed by loading the start material at a flow rate of 1 ml/min. This was followed by a wash step with the equilibration buffer and then the column was eluted using the eluting buffer. Samples were withdrawn and analysed for rhG-CSF by a HPLC method. The analysis showed that rhG-CSF bound to the CAPTO® MMC resin during these buffer conditions. As seen in Table 5 no rhG-CSF was found in the flow through. The eluting buffer was altered to a buffer containing arginine and no sodium chloride and the pH was 4.0, the same as in the equilibration buffer. No rhG-CSF was found in the eluted fraction. This means a higher arginin concentration (1M) did not have any effect on the elution of rhG-CSF from the CAPTO® MMC column. But as seen in FIG. 3 a peak was obtained when the column was eluted by the eluting buffer containing 1M arginin and pH 4. The second large peak is a result of 1M NaOH wash.

TABLE 5

| Sample | Volume ml | rhG-CSF µg/ml | Total rhG-CSF µg | Yield % |
|---|---|---|---|---|
| Start material | 9.04 | 79.98 | 723 | 100 |
| Flow through and equil. wash | 18 | 0 | 0 | 0 |
| Eluate | 9 | 0 | 0 | 0 |

Conclusion rhG-CSF could not be eluted from the CAPTO® MMC resin only by adding 1M arginine mono hydrochloride to the buffer, without changing the pH. This can work as a wash step.
Figure Legend FIG. 3.

Experiment 5; A chromatogram of the G-CSF purification on a CAPTO® MMC column at pH 4.0 using a sodium acetate buffer. The absorbance at 280 nm (mAU) and the conductivity (mS/cm) measured are presented in the figure. The column was eluted using a buffer with pH 4.0 containing 1M arginine mono hydrochloride. A double peak was obtained by the elution. A single peak was obtained in the eluate fraction. A large peak was obtained by the 1M NaOH wash.

Example 6 (Experiments 6, 7, 8, 9, 10, 11)

Start Material

Purified rhG-CSF was diluted in an equilibration buffer to lower the total protein concentration and to achieve a more convenient volume prior to be loaded on a CAPTO® MMC column. And also to achieve the pH that was requested for each experiment. The rhG-CSF was prior to dilution dissolved in 20 mM sodium acetate, 0.2M NaCl, 0.02% TWEEN® 20, pH 6.5.

Chromatographic Resin and Column

CAPTO® MMC, a mixed mode resin from GE Healthcare (cat no. 17-5317), was used as capture step for the rhG-CSF molecule. CAPTO® MMC is a weak cationic resin with hydrophobic and thiophilic interactions and hydrogen bonding. A TRICORN® 5/150 column (GE Healthcare) was packed with CAPTO® MMC resin to a bed height of 15 cm. The column volume (CV) of CAPTO® MMC was 3 ml.

Buffers

Experiment 6

Equilibration buffer: 20 mM sodium acetate, 0.1M NaCl, 0.02% Polysorbate 80, pH 4.0
Wash buffer: 20 mM NaAc, 1M NaCl, 0.02% Polysorbate 80, pH 4.0
Eluting buffer: 20 mM sodium citrate, 0.5M arginine mono hydrochloride, 0.1M NaCl, 0.02% Polysorbate 80, pH 7.0.

Experiment 7

Equilibration buffer: 20 mM sodium citrate, 0.1M NaCl, 0.02% Polysorbate 80, pH 5.0
Eluting buffer: 20 mM sodium citrate, 0.5M arginine mono hydrochloride, 0.1M NaCl, 0.02% Polysorbate 80, pH 7.0.

Experiment 8

Equilibration buffer: 20 mM sodium citrate, 0.1M NaCl, 0.02% Polysorbate 80, pH 6.0
Eluting buffer: 20 mM sodium citrate, 0.5M arginine mono hydrochloride, 0.1M NaCl, 0.02% Polysorbate 80, pH 7.0.

Experiment 9

Equilibration buffer: 20 mM sodium citrate, 0.1M NaCl, 0.02% Polysorbate 80, pH 6.5
Eluting buffer: 20 mM sodium citrate, 0.5M arginine mono hydrochloride, 0.1M NaCl, 0.02% Polysorbate 80, pH 7.0.

Experiment 10

Equilibration buffer: 20 mM sodium citrate, 0.1M NaCl, 0.02% Polysorbate 80, pH 5.5
Eluting buffer: 20 mM sodium citrate, 0.5M arginine mono hydrochloride, 0.1M NaCl, 0.02% Polysorbate 80, pH 7.0.

Experiment 11

Equilibration buffer: 20 mM sodium citrate, 0.1M NaCl, 0.02% Polysorbate 80, pH 4.0
Eluting buffer: 20 mM sodium citrate, 0.5M arginine mono hydrochloride, 0.1M NaCl, 0.02% Polysorbate 80, pH 7.0.

Experimental Setup

Each experiment was performed as follows. The purified rhG-CSF was diluted approximately 1 in 20 with the equilibration buffer to be used. The pH of the start material was controlled and was in all experiments the same as the equilibration buffer without being adjusted. The column was equilibrated with equilibration buffer followed by loading the start material at a flow rate of 1 ml/min. This was followed by a wash step with the equilibration buffer and then the column was eluted using the eluting buffer. In experiment 6 the column was also washed with a buffer containing 1M NaCl prior to elution. Samples were withdrawn and analysed for rhG-CSF by an HPLC method.

Figure 4:
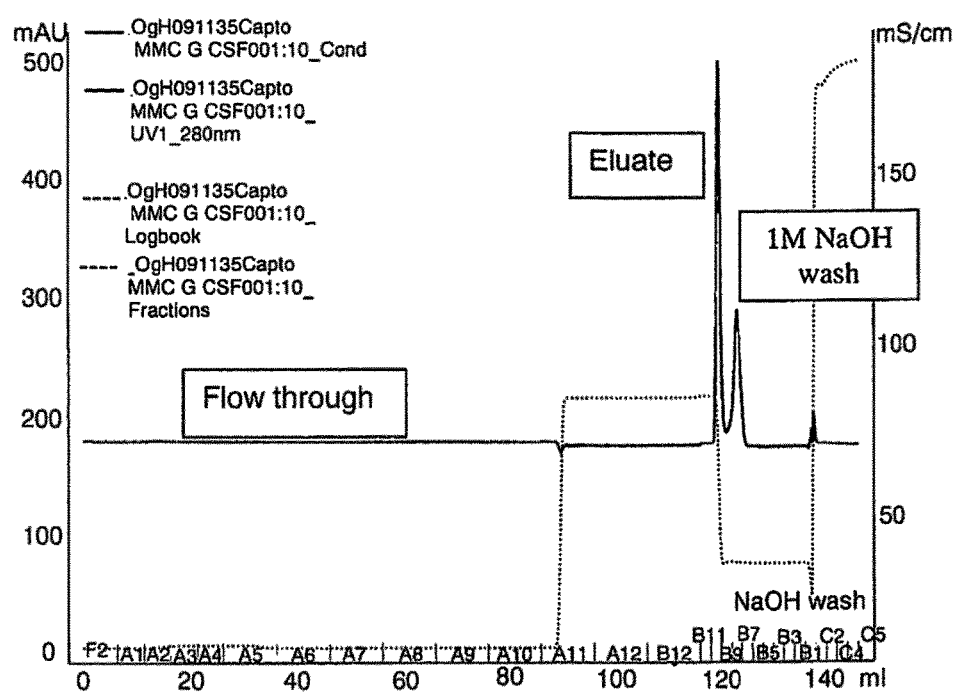
FIG. 4 shows a chromatogram of the G-CSF purification on a CAPTO® MMC column at pH 4.0 of the start material using a sodium acetate buffer.

As seen FIG. 4 in Experiment 6 no peak was obtained in the 1M NaCl wash, which indicate that no rhG-CSF was washed out from the CAPTO® MMC column. The same elution profile was obtained when G-CSF was purified on a CAPTO® MMC column independent if a sodium acetate buffer or sodium citrate buffer at pH 4 was used (Experiment 6 and Experiment 11)

The results of the analysis to show at which level rhG-CSF binds to CAPTO® MMC and which yield that is obtained is presented in table 6.

TABLE 6

| Exp. No. Experiment | pH on the load sample | G-CSF in the Flow through % | G-CSF in the Eluate % | FIG. |
|---|---|---|---|---|
| 6 | 4.0 | 0 | 105 | 4 |
| 11 | 4.0 | 0 | 100 | 5 |
| 7 | 5.0 | 0 | 98 | 6 |
| 10 | 5.5 | 0 | 97 | 7 |
| 8 | 6.0 | 0 | 97 | 8 |
| 9 | 6.5 | 26.8 | 25.7 | 9 |

The data from table 6 shows that G-CSF binds to the CAPTO® MMC resin at pH 4 to 6 without any loss of material in the flow through. But with pH 6.5 on the start material, a majority of the G-CSF detected, was found in the flow through fraction.

The CAPTO® MMC column was eluted with a buffer set at pH 7 and containing 0.5M arginine. The G-CSF recovery was high when the material was loaded to the column at pH 4 to 6, while when pH 6.5 was used on the start material the yield in the eluate was low.

Figure 5:
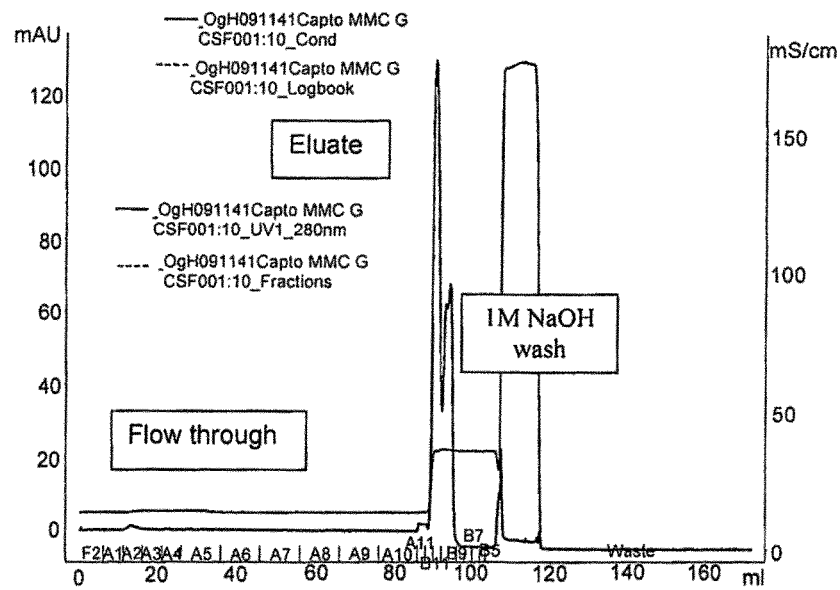
FIG. 5 shows a chromatogram of the G-CSF purification on a CAPTO® MMC column at pH 4.0 using a sodium citrate buffer.
Figure 6:
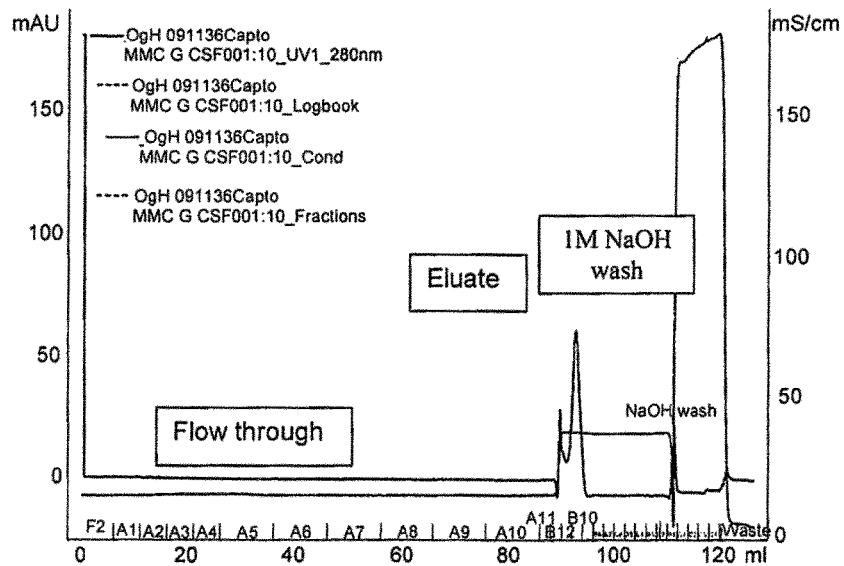
FIG. 6 shows a chromatogram of the G-CSF purification on a CAPTO® MMC column at pH 5.0 using a sodium citrate buffer.
Figure 7:
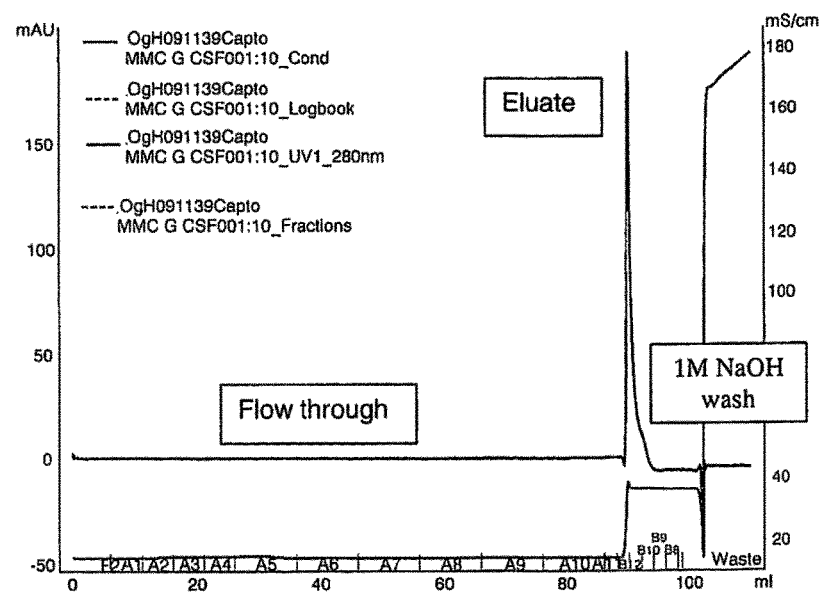
FIG. 7 shows a chromatogram of the G-CSF purification on a CAPTO® MMC column at pH 5.5 using a sodium citrate buffer.
Figure 8:
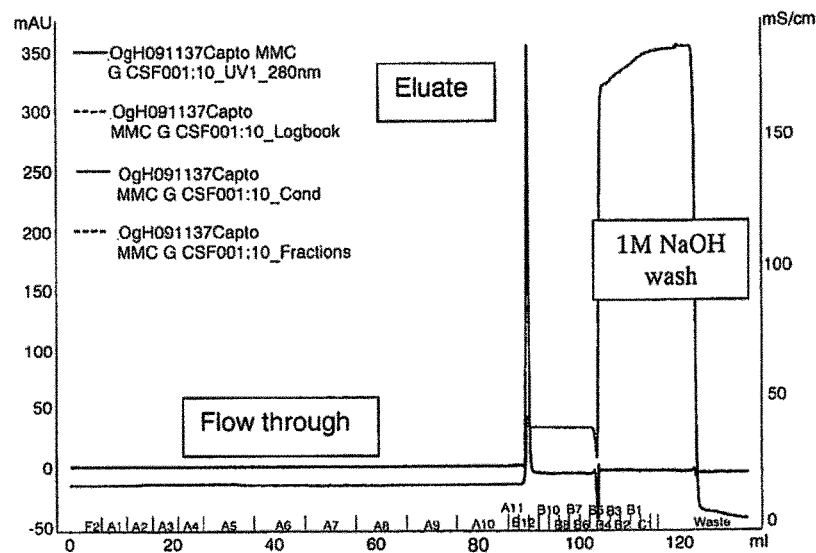
FIG. 8 shows a chromatogram of the G-CSF purification on a CAPTO® MMC column at pH 6.0 using a sodium citrate buffer.
Figure 9:
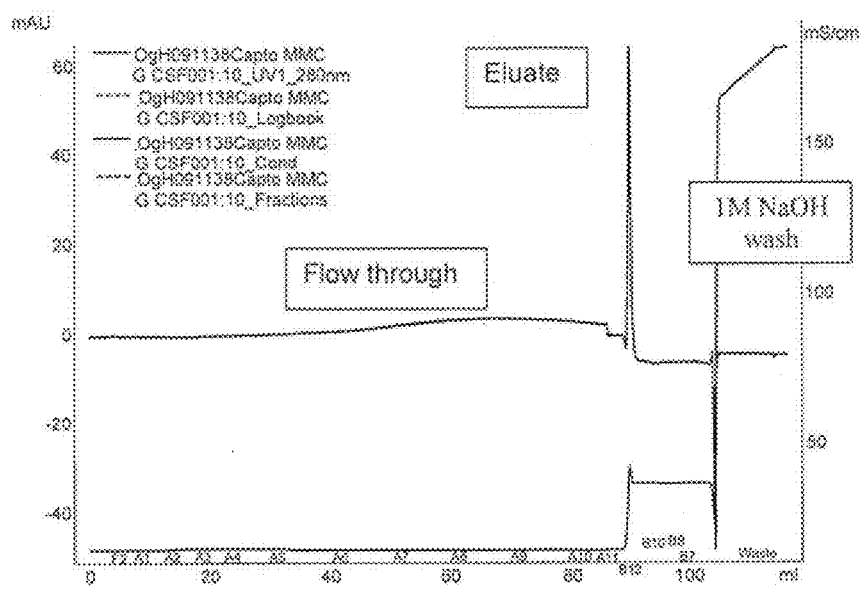
FIG. 9 shows a chromatogram of the G-CSF purification on a CAPTO® MMC column at pH 6.5 using a sodium citrate buffer.

In the chromatograms below (FIGS. 4, 5 and 6) it is shown that when rhG-CSF is in a buffer with pH 4 or 5 it is eluted from a CAPTO® MMC column as a double peak. While a single peak was obtained when the pH of the start material was 5.5, 6.0 or 6.5 (FIGS. 7, 8 and 9). As shown on the silver stained SDS PAGE (FIG. 10A) the eluate from Experiment 8 (pH 6.0), Experiment 9 (pH 6.5) and Experiment 10 (pH 5.5) have a nice single band. While the eluate from Experiment 6 (pH 4.0) and Experiment 7 (pH 5.0) shows more bands on the silver stained SDS-PAGE (FIG. 10B).

Conclusion

The results from these experiments shows that rhG-CSF can bind to CAPTO® MMC at pH 4.0, 5.0, 5.5, 6.0. The rhG-CSF binding to CAPTO® MMC at pH 6.5 is less strong and rhG-CSF was found in the flow through fraction which was not the case at pH 4 to 6.

The elution profile is better when pH 5.5 to 6.5 was used and the product looks better on an SDS-PAGE when these pH was used on the loading material.

Due to the leakage of G-CSF on the CAPTO® MMC column when pH 6.5 was used, pH 5.5 to 6.0 on the loading material is preferably used.

The bound material was eluted at pH 7 in all experiments, and the peak got more concentrated when 0.5M arginine mono hydrochloride was included in the eluting buffer. A 1M NaCl wash can be performed at pH 4 without any loss of G-CSF.

Figure Legends for FIG. 4-10

FIG. 4.

Experiment 6; A chromatogram of the G-CSF purification on a CAPTO® MMC column at pH 4.0 of the start material using a sodium acetate buffer. The absorbance at 280 nm (mAU) and the conductivity (mS/cm) measured are presented in the figure. The column was eluted using a buffer with pH 7.0 containing 0.5M arginine mono hydrochloride. A double peak was obtained by the elution. The double peak was collected as one fraction.

FIG. 5.

Experiment 11; A chromatogram of the G-CSF purification on a CAPTO® MMC column at pH 4.0 using a sodium citrate buffer. The absorbance at 280 nm (mAU) and the conductivity (mS/cm) measured are presented in the figure. The column was eluted using a buffer with pH 7.0 containing 0.5M arginine mono hydrochloride. A double peak was obtained by the elution. The double peak was collected as one fraction.

FIG. 6.

Experiment 7; A chromatogram of the G-CSF purification on a CAPTO® MMC column at pH 5.0 using a sodium citrate buffer. The absorbance at 280 nm (mAU) and the conductivity (mS/cm) measured are presented in the figure. The column was eluted using a buffer with pH 7.0 containing 0.5M arginine mono hydrochloride. A double peak was obtained by the elution. The double peak was collected as one fraction.

FIG. 7.

Experiment 10; A chromatogram of the G-CSF purification on a CAPTO® MMC column at pH 5.5 using a sodium citrate buffer. The absorbance at 280 nm (mAU) and the conductivity (mS/cm) measured are presented in the figure. The column was eluted using a buffer with pH 7.0 containing 0.5M arginine mono hydrochloride. One slightly non-uniformed peak was obtained by the elution.

FIG. 8.

Experiment 8; A chromatogram of the G-CSF purification on a CAPTO® MMC column at pH 6.0 using a sodium citrate buffer. The absorbance at 280 nm (mAU) and the conductivity (mS/cm) measured are presented in the figure. The column was eluted using a buffer with pH 7.0 containing 0.5M arginine mono hydrochloride. One concentrated uniform peak was obtained.

FIG. 9.

Experiment 9; A chromatogram of the G-CSF purification on a CAPTO® MMC column at pH 6.5 using a sodium citrate buffer. The absorbance at 280 nm (mAU) and the conductivity (mS/cm) measured are presented in the figure. The column was eluted using a buffer with pH 7.0 containing 0.5M arginine mono hydrochloride. One concentrated uniform peak was obtained.

Figure 10A:
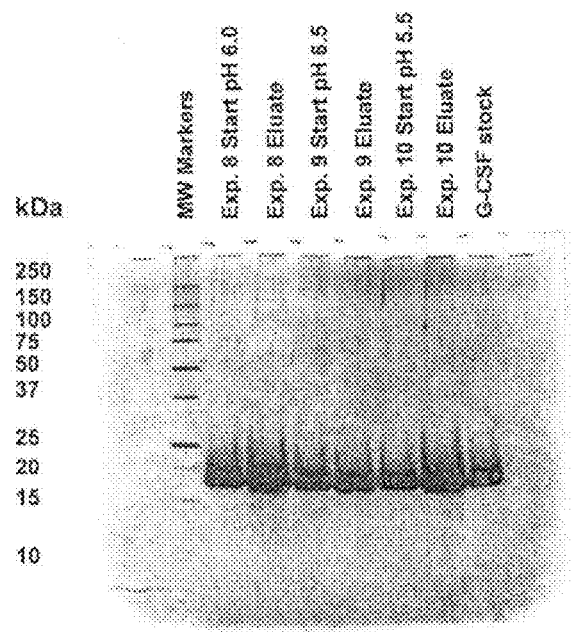
FIGS. 10A and 10B show a silver stained SDS-PAGE and the separation of proteins in the start and eluate from the CAPTO® MMC.
Figure 10B:
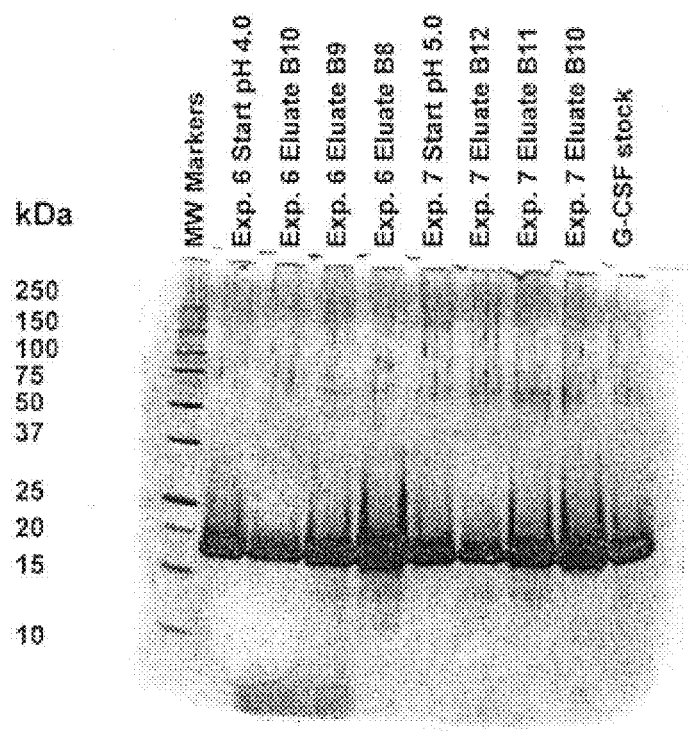

FIG. 10A and FIG. 10B

Experiment 6, 7, 8, 9, 10; Separation of proteins in the start and eluate from the CAPTO® MMC experiments where different pH values was used in the start material. The samples are reduced (SDS treated) and separated on a 10% polyacryl amide gel. The proteins are the visualized by a silver staining.

Example 7 (Experiment 12)

Start Material

Recombinant human G-CSF produced in HEK 293 cells. The cells were removed and the cell free supernatant was the start material loaded onto the CAPTO® MMC column.

Chromatographic Resin and Column

CAPTO® MMC, a mixed mode resin from GE Healthcare (cat no. 17-5317), was used as capture step for the rhG-CSF molecule. CAPTO® MMC is a weak cationic resin with hydrophobic and thiophilic interactions and hydrogen bonding. An XK16 column (GE Healthcare) was packed with CAPTO® MMC resin to a bed height of 13.5 cm. The column volume (CV) of CAPTO® MMC was 27 ml.

Buffers

Equilibration buffer: 20 mM sodium citrate, 0.1M NaCl, 0.02% Polysorbate 80, pH 6.0

Eluting buffer: 20 mM sodium citrate, 0.1M NaCl, 0.5M arginin mono hydrochloride, 0.02% Polysorbate 80, pH 7.0.

Experimental Setup

The pH of the cell free supernatant was adjusted to 6.0. The column was equilibrated with equilibration buffer followed by loading the pH adjusted start material at a flow rate of 13.5 ml/min. This was followed by a wash step with the equilibration buffer and then the column was eluted using the eluting buffer. Samples were withdrawn and analysed for rhG-CSF by a HPLC method. The analysis showed that all rhG-CSF loaded onto the column bound to the CAPTO® MMC resin during these buffer conditions, no G-CSF was found in the flow through fraction. The eluting buffer contained 20 mM NaCitrate, 0.5M arginine, 0.1M NaCl and 0.02% Polysorbate 80, and the pH was 7.0. The elution of the bound proteins to the CAPTO® MMC resin resulted in a main peak and a small second peak. All G-CSF loaded onto the CAPTO® MMC column was found in the main peak and no G-CSF was detected in the second small peak (FIG. 11).

Conclusion

Recombinant human G-CSF in cell free cultured medium bound to a CAPTO® MMC resin at pH 6.0.
No G-CSF was found in the flow through fraction.
The bound material was eluted from the CAPTO® MMC resin by altering the pH to 7 and by adding 0.5M arginine to concentrate the elution peak.

Figure 11:
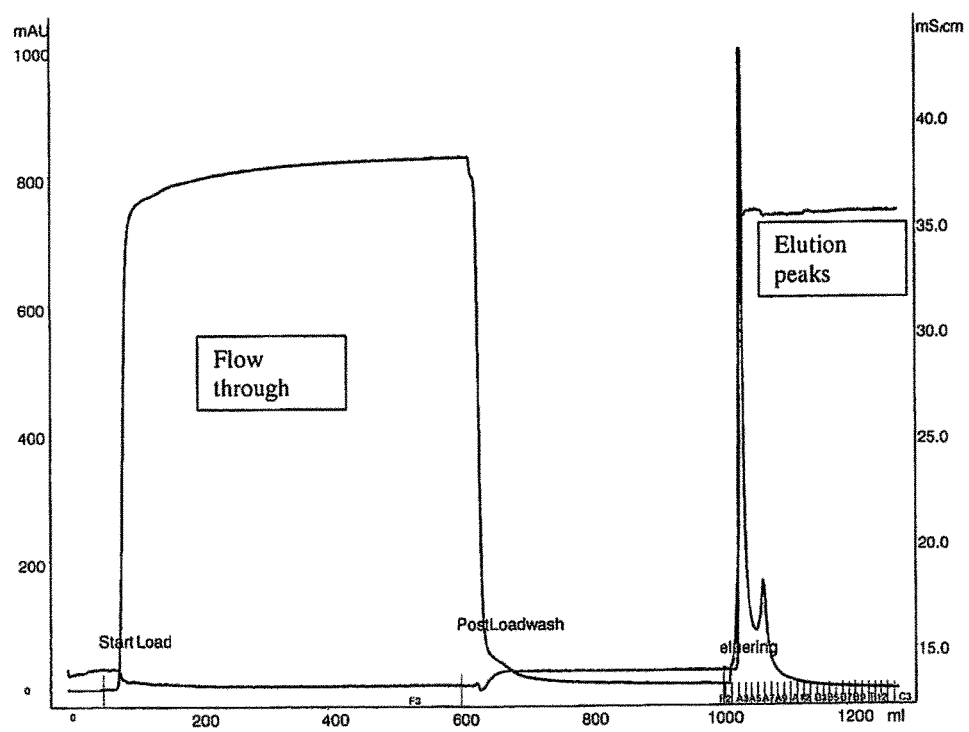
FIG. 11 shows a chromatogram of the G-CSF purification from a cell free supernatant.

Figure Legend FIG. 11

Experiment 12; A chromatogram of the G-CSF purification from a cell free supernatant on a CAPTO® MMC column at pH 6.0 using a sodium citrate buffer. The absorbance at 280 nm (mAU) and the conductivity (mS/cm) measured are presented in the figure. The column was eluted using a buffer with pH 7.0 containing 0.5M arginine mono hydrochloride. A double peak was obtained but G-CSF was only found in the main peak.

Example 8

Column and Resin

A TRICORN® 5/50 column (GE Healthcare) was packed with a yeast derived $F_{ab}$ fragment based affinity ligand coupled to a CAPTO® MP base matrix. The bed height was approximately 2 cm, giving a resin volume of app. 0.4 ml. The affinity resin prototype (G-CSF8) was obtained from BAC BV.

Starting Material

The starting material used was a G-CSF containing cell supernatant produced in HEK293F cells.

Buffer Compositions:

Buffer a (Equilibration Buffer)
0.3M NaCl, 0.02M Na-citrat, 0.02% TWEEN® 20, pH 6.0, conductivity 32 mS/cm at +25° C.

Buffer B (Elution Buffer I)
0.3M NaCl, 0.02M Na-citrat, 0.02% TWEEN® 20, pH 3.0, conductivity 32 mS/cm at +25° C.

The column was equilibrated with equilibration buffer A followed by loading of the starting material. The resin was thereafter washed with equilibration buffer A and the bound G-CSF was subsequently eluted with elution buffer B. The G-CSF content in the starting material and eluate were analyzed (Table 7).

TABLE 7

Results from G-CSF affinity resin experiment, elution with pH 3

| Sample | Volume (ml) | G-CSF (ug/ml) | Total amount G-CSF (ug) | Yield (%) |
|---|---|---|---|---|
| Starting material (load) | 100 | 2 | 200 | 100 |
| Eluate (Buffer B) | 1.5 | 111 | 170 | 83 |

Figure 12:
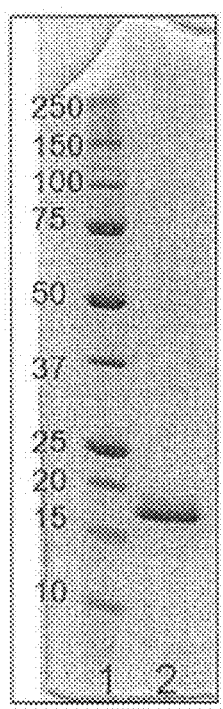
FIG. 12 shows a Coomassie stained SDS-PAGE showing the eluate after the affinity chromatography step.

FIG. 12 shows a Coomassie stained SDS-PAGE showing the eluate after the affinity chromatography step.

Lane Sample
1 Molecular weight standard
2 Eluate (Example 8)

Conclusion Example 8

Excellent purity and recovery was achieved when using a low pH buffer (pH 3) for elution of G-CSF.

Example 9

Column and Resin

A TRICORN® 5/50 column (GE Healthcare) was packed with a yeast derived $F_{ab}$ fragment based affinity ligand coupled to a CAPTO® MP base matrix. The bed height was approximately 2 cm, giving a resin volume of app. 0.4 ml. The affinity resin prototype (G-CSF8) was obtained from BAC BV.

Starting Material

The starting material used was a G-CSF containing cell supernatant from HEK293F cells.

Buffer Compositions:

Buffer a (Equilibration Buffer)
0.3M NaCl, 0.02M Na-citrat, 0.02% TWEEN® 20, pH 6.0, conductivity 32 mS/cm at +25° C.

Buffer C (Elution Buffer II)
1.0M NaCl, 0.02M Na-citrat, 0.8M Arg, 0.02% TWEEN® 20, pH 6.0, conductivity 89 mS/cm at +25° C.

The equilibration and elution buffers are not limited to the stated pH, concentrations, and type of buffer, salts or detergent.

The column was equilibrated with equilibration buffer A followed by loading of the starting material. The resin was thereafter washed with equilibration buffer A and the bound G-CSF was subsequently eluted with elution buffer C. The G-CSF content in the starting material and eluate were analyzed (Table 8).

TABLE 8

Results from G-CSF affinity resin experiment, elution with arginine

| Sample | Volume (ml) | G-CSF (ug/ml) | Total amount G-CSF (ug) | Yield (%) |
|---|---|---|---|---|
| Starting material (load) | 100 | 2 | 200 | 100 |
| Eluate (Buffer B) | 3.7 | 30 | 110 | 56 |

Conclusion Example 9

It is possible to elute G-CSF from the affinity column using a mixture of sodium chloride and arginine.

Example 10

Column and Resin

A TRICORN® 5/50 column (GE Healthcare) was packed with a yeast derived $F_{ab}$ fragment based affinity ligand coupled to a CAPTO® MP base matrix. The bed height was approximately 2 cm, giving a resin volume of app. 0.4 ml. The affinity resin prototype (G-CSF8) was obtained from BAC BV.

Starting Material

The starting material used was a G-CSF containing cell supernatant from HEK293F cells.

Buffer Compositions:

Buffer A (Equilibration Buffer)

0.3M NaCl, 0.02M Na-citrat, 0.02% TWEEN® 20, pH 6.0, conductivity 32 mS/cm at +25° C.

Buffer D (Elution buffer III) 2.0M MgCl2, 0.02M Tris, 0.02% TWEEN® 20, pH 7.5, conductivity 144 mS/cm at +25° C.

The equilibration and elution buffers are not limited to the stated pH, concentrations, and type of buffer, salts or detergent.

The column was equilibrated with equilibration buffer A followed by loading of the starting material. The resin was thereafter washed with equilibration buffer A and the bound G-CSF was subsequently eluted with elution buffer D. The G-CSF content in the starting material and eluate were analyzed (Table 9).

TABLE 9

Results from G-CSF affinity resin experiment, elution with MgCl2

| Sample | Volume (ml) | G-CSF (ug/ml) | Total amount G-CSF (ug) | Yield (%) |
|---|---|---|---|---|
| Starting material (load) | 100 | 12 | 1200 | 100 |
| Eluate (Buffer B) | 2.5 | 390 | 970 | 81 |

Conclusion Example 10

It is possible to elute G-CSF from the affinity column using 2 M MgCl2 as eluent.

Example 11

Column and Resin

TRICORN® 5/50 columns (GE Healthcare) was packed with 3 different yeast derived $F_{ab}$ fragment based affinity ligand prototypes, coupled to a CAPTO® MP base matrix. The bed height was approximately 2 cm, giving a resin volume of app. 0.4 ml. The affinity resin prototypes (G-CSF2, G-CSF3 and G-CSF6) were obtained from BAC BV.

Starting Material

The starting material used was a G-CSF containing cell supernatant from HEK293F cells.

Buffer Compositions:

Buffer a (Equilibration Buffer)

0.3M NaCl, 0.02M Na-citrat, 0.02% TWEEN® 20, pH 6.0, conductivity 32 mS/cm at +25° C.

Buffer B (Elution buffer I)

0.3M NaCl, 0.02M Na-citrat, 0.02% TWEEN® 20, pH 3.0, conductivity 32 mS/cm at +25° C.

The columns were equilibrated with equilibration buffer A followed by loading of the starting material. The resins were thereafter washed with equilibration buffer A and the bound G-CSF was subsequently eluted with elution buffer B. The G-CSF content in the starting material, flow through fractions and eluates were analyzed (Table).

TABLE 10

Results from G-CSF affinity resin experiment, test of different affinity ligand prototypes, elution with pH 3

| Sample | Volume (ml) | G-CSF (ug/ml) | Total amount G-CSF (ug) | Yield (%) |
|---|---|---|---|---|
| Ligand G-CSF2 | | | | |
| Starting material (load) | 100 | 10 | 1100 | 100 |
| Flow through fraction | 112.5 | 4 | 500 | 45 |
| Eluate (Buffer B) | 2 | 290 | 570 | 57 |
| Ligand G-CSF3 | | | | |
| Starting material (load) | 100 | 11 | 1100 | 100 |
| Flow through fraction | 112.5 | 0 | 0 | 0 |
| Eluate (Buffer B) | 2 | 510 | 1020 | 93 |
| Ligand G-CSF6 | | | | |
| Starting material (load) | 100 | 12 | 1200 | 100 |
| Flow through fraction | 112.5 | 2 | 200 | 19 |
| Eluate (Buffer B) | 1.5 | 450 | 670 | 56 |

Figure 13:
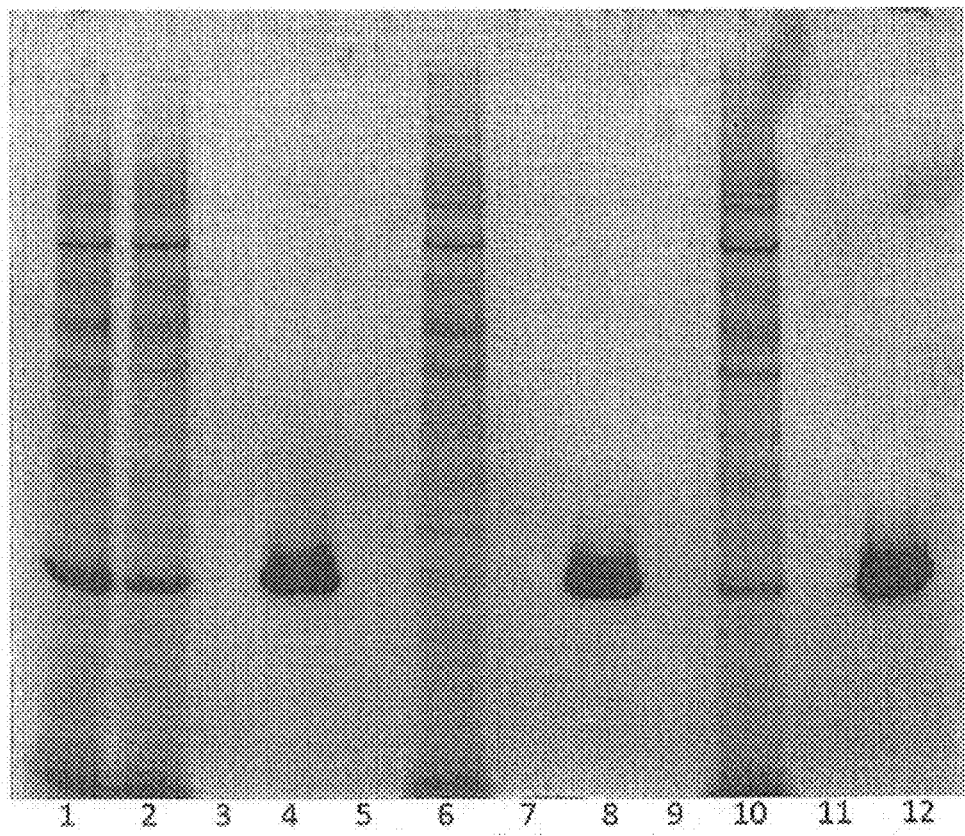
FIG. 13 shows a silver stained SDS-PAGE showing starting material, flow through and eluates after the affinity chromatography step.

FIG. 13 shows a silver stained SDS-PAGE showing starting material, flow through and eluates after the affinity chromatography step.

Legend:
Lane Sample
1 G-CSF2 start; 2 G-CSF2 flow through; 3 Blank; 4 G-CSF2 eluate; 5. Blank; 6 G-CSF3 flow through; 7 Blank; 8 G-CSF3 eluate; 9. Blank; 10 G-CSF6 flow through; 11 Blank 12 G-CSF6 eluate Conclusion Example 11

Different affinity ligand prototypes gives different binding capacity of G-CSF, as shown by the detection of G-CSF in the flow through and the varying recovery in the elution fraction using low pH as eluent. However, as shown in FIG. 13, all affinity ligand gives the same excellent purity profile in the eluate.

The invention claimed is:

1. A process of purifying a Growth Factor Protein Granulocyte Colony Stimulating Factor (G-CSF) in a purification sequence employing chromatography comprising:
   performing at least one chromatography step using a multimodal resin which comprises a negatively charged 2-(benzoylamino) butanoic acid ligand,
   binding the G-CSF to the multimodal resin at a pH from 4 to 6.2, and
   eluting the G-CSF at a pH in the range of from 5.5 to 6.5, wherein the elution is performed with an arginine buffer having a concentration in the range of from 0.1 M to 2.0 M,
   optionally in combination with an affinity ligand chromatography step wherein the affinity ligand is a yeast derived $F_{ab}$ fragment directed toward the G-CSF.

2. The process of claim 1, wherein the multimodal resin comprises moieties bound to a matrix and the moieties are able to interact with the G-CSF in a mixture by ionic interactions, hydrogen bonding, and/or hydrophobic interaction.

3. The process of claim 2, wherein the mixture comprising the G-CSF is a solution.

4. The process of claim 1, wherein the G-CSF is a recombinant G-CSF.

5. The process of claim 1, wherein the G-CSF binds to the multimodal resin at pH 4.0 to pH 6.0, and the G-CSF is eluted from the multimodal resin at pH 6.5.

6. The process of claim 1, wherein the binding and/or elution steps are carried out in a buffering substance comprising sodium citrate, sodium acetate, or 2-(4-(2-Hydroxyethyl)-1-piperazinyl)-ethane sulfonic acid (HEPES).

7. The process of claim 6, wherein a non-ionic detergent is present in any of the buffers.

8. The process of claim 1, wherein a buffer comprising about 0.1 M to about 2 M sodium chloride or about 0.1 M to about 2 M arginine mono hydrochloride is used in a wash-step at a pH range of 4.0 to 6.0 prior to elution of the G-CSF.

9. The process of claim 1, further comprising applying a wash buffer to the multimodal resin, to wash away contaminants and retain the G-CSF, before the G-CSF is eluted, wherein the wash buffer comprises an amino acid having a basic side chain and/or a salt.

10. The process of claim 1, wherein the purification sequence further comprises one or more of the following steps:
   subjecting the G-CSF to a chemically based inactivation step for enveloped viruses;
   binding and elution from an affinity resin comprising as an affinity ligand a yeast derived $F_{ab}$ fragment directed toward the G-CSF;
   binding and elution from a cation exchanger;
   subjecting the G-CSF to a pathogen filtration removal step with a filter having a mean pore size of about 20 nm;
   subjecting the G-CSF to a buffer exchange and/or concentrating step comprising ultra-filtration with an approximate cut off value of between 1 and 5 kDa; and
   subjecting the G-CSF to a size exclusion chromatography resin.

11. The process claim 10, wherein the purity of the product resulting from the affinity chromatography step is more than 90%.

12. The process claim 11, wherein additional chromatography step(s) is/are performed, selected from size exclusion, anion exchange, cation exchange, hydrophobic interaction and immobilized metal affinity chromatography, wherein the purity of the final product is more than 99%.

13. The process of claim 1, wherein the purification sequence further comprises pathogen removal and/or inactivation steps.

14. The process of claim 1, comprising subjecting the G-CSF to a chromatography step using as an affinity ligand a yeast derived $F_{ab}$ fragment directed toward the G-CSF.

15. The process of claim 1, wherein the binding step is carried out in a buffer comprising at least one of the buffering substances selected from the group consisting of sodium citrate, histidine, 2-(4-(2-Hydroxyethyl)-1-piperazinyl)-ethane sulfonic acid (HEPES), 2-(N-Morpholino)ethane sulfonic acid (MES), Tris base and sodium acetate.

16. The process of claim 7, wherein the non-ionic detergent is selected from the group consisting of Polysorbate 20, Polysorbate 40, Polysorbate 60, and Polysorbate 80.

17. The process of claim 1, wherein the arginine buffer further comprises at least one of the buffering substances selected from the group consisting of sodium citrate, histidine, 2-(4-(2-Hydroxyethyl)-1-piperazinyl)-ethane sulfonic acid (HEPES), 2-(N-Morpholino)ethane sulfonic acid (MES), Tris base and sodium acetate.

* * * * *